United States Patent [19]

Buzby, Jr. et al.

[11] Patent Number: 4,794,196
[45] Date of Patent: Dec. 27, 1988

[54] N-AMINOALKYLPERFLUOROALK-ANOYLAMINOBENZENE-SULFONAMIDE ANTI-ARRHYTHMIC AGENTS

[75] Inventors: George C. Buzby, Jr., Blue Bell; Thomas J. Colatsky, Paoli, both of Pa.

[73] Assignee: American Home Products Corporation, New York, N.Y.

[21] Appl. No.: 12,969

[22] Filed: Feb. 10, 1987

[51] Int. Cl.$^4$ .................. C07C 143/80; A61L 31/18
[52] U.S. Cl. .................. 564/86; 260/501.1; 260/501.21; 260/543 R
[58] Field of Search .......................... 564/86

[56] References Cited

U.S. PATENT DOCUMENTS

| 2,233,296 | 4/1941 | Nelles et al. | 564/96 |
| 3,580,949 | 5/1971 | Gruenman et al. | 564/96 |
| 4,698,445 | 10/1987 | Buzby et al. | 564/86 |

FOREIGN PATENT DOCUMENTS

| 1912848 | 10/1969 | Fed. Rep. of Germany | 564/86 |
| 7237413 | 9/1972 | Japan | 564/86 |
| 1053204 | 12/1966 | United Kingdom | 564/86 |

OTHER PUBLICATIONS

Silberg et al., ACAD Rep Populace Romire, Fillala Clug, Studee Cercetari Med., 10 241–252 (1959).
Bexton et al., Pharmac. Ther. 17, 315–55 (1982).
Vaughan-Williams, J. Clin. Pharmacol. 24, 129–47 (1984).
Thomis et al., Ann. Rep. Med. Chem. 18, 99–108 (1983).
Fleckenstein, Ann. Rev. Pharmacol., 17, 149–66 (1977).
Riccieri et al., Chem. Abstracts, vol. 56, 5954e (1962).
Wohl et al., 192nd ACS Nat'l. Mtg., Anaheim, Calif., Sep. 7–12, 1986, Abstracts of Papers, Abstract No. 9.

*Primary Examiner*—Floyd D. Higel
*Attorney, Agent, or Firm*—Richard K. Jackson

[57] ABSTRACT

N-Aminoalkyl(perfluoroalkanoylaminophenyl)sulfonic acid amides of the formula:

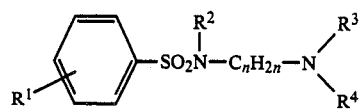

in which $R^1$ is perfluoroalkanoylamino of 2 to 4 carbon atoms, in 3- or 4- position of the benzene ring;

$R^2$ is hydrogen or alkyl of 1 to 4 carbon atoms;

$R^3$ is hydrogen or straight or branched chain alkyl of 1 to 4 carbon atoms;

$R^4$ is straight or branched chain alkyl of 1 to 4 carbon atoms; and n is one of the integers 2, 3 or 4;

or a pharmaceutically acceptable salt thereof, are Class I anti-arrhythmic agents useful in the treatment of cardiac arrhythmias and conditions characterized by coronary arteries vasospasm and myocardial ischemia.

6 Claims, No Drawings

N-AMINOALKYLPERFLUOROALK-ANOYLAMINOBENZENE-SULFONAMIDE ANTI-ARRHYTHMIC AGENTS

RELATED APPLICATIONS

U.S. patent application Ser. No. 875,816 filed by George C. Buzby, Jr. and Thomas J. Colatsky on June 18, 1986, now U.S. Pat. No. 4,698,445 discloses and claims, among other things, certain alkanoylamino-N-[aminoalkyl]benzenesulfonamide derivatives possessing Class III anti-arrhythmic activity.

BACKGROUND OF THE INVENTION

Cardiac arrhythmias can be treated effectively by agents which slow conduction and/or prolong refractoriness in the heart. Class I anti-arrhythmics have their predominant effects on conduction velocity, with more modest effects on refractory period, while Class III anti-arrhythmic agents significantly prolong refractoriness without greatly altering intracardiac conduction. The electrophysiologic properties of a compound defining a Class III activity profile are observed in vivo as negligible effects on atrial, ventricular and H-V conduction time while producing a marked increase (greater than 20 percent) in both the atrial and ventricular refractory period. In contrast, Class I agents will demonstrate a marked rate-dependent slowing of ventricular conduction velocity with changes in the refractory period generally less than twenty percent (20%). Recent reviews of these agents are by Anderson, Fed. Proc. 45, 2213-2219 (1986); Bexton et al., Pharmac. Thera. 17, 315-55 (1982); Vaughan-Williams, J. Clin. Pharmacol. 24, 129-47 (1984) and Thomis et al., Ann. Rep. Med. Chem. 18, 99-108 (1983).

DESCRIPTION OF THE INVENTION

In accordance with this invention there is provided a group of anti-arrhythmic agents of the formula:

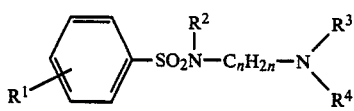

in which $R^1$ is perfluoroalkanoylamino of 2 to 4 carbon atoms, in 3- or 4-position of benzene ring;

$R^2$ is hydrogen or alkyl of 1 to 4 carbon atoms;

$R^3$ is hydrogen or straight or branched chain alkyl of 1 to 4 carbon atoms;

$R^4$ is straight or branched chain alkyl of 1 to 4 carbon atoms; and n is one of the integers 2, 3 or 4;

or a pharmaceutically acceptable salt thereof.

The pharmaceutically acceptable salts of the anti-arrhythmic agents of this inventon are prepared directly by neutralization of the free base. These physiologically acceptable salts may be formed with organic or inorganic acids such as hydrochloric, hydrobromic, phosphoric, sulfuric, sulfamic, nitric, methylsulfonic, acetic, maleic, succinic, fumaric, tartaric, citric, salicylic, lactic, naphthalenesulfonic acid, and the like.

The compounds of this invention are prepared by reaction of a perfluoroalkanoylamino-benzene sulfonyl halide with an appropriately substituted α, ω-alkane diamine of 2 to 4 carbon atoms. Direct acylation of an appropriately substituted amino-N-[aminoalkyl]benzenesulfonamide with a perfluoroalkanoyl halide or anhydride in the presence of an acid binding agent such as triethylamine provides an alternative method of synthesis of the compounds of this invention. These reactants are generally known compounds and otherwise are routinely prepared by techniques well within the skill of the medicinal chemist.

The compounds of this invention demonstrate both Class I anti-arrhythmic activity and Class III activity when tested in the standard experimental animal in accordance with the following procedure:

Bundles of free-running Purkinje fibers with attached myocardium obtained from either ventricle of adult dog heart were pinned without stretching to the bottom of a 10 ml tissue chamber and continuously superfused with oxygenated Tyrode's solution at a flow rate of 10 ml/min. The composition of the Tyrode's solution was (mM): NaCl 150; KCl 4,0; $CaCl_2$ 2.7; $MgCl_2$ 0.5; HEPE buffer (7.4) 10; dextrose 5.5. The solution was aerated with 100% $O_2$. Bath temperature was maintained at $36\pm0.5°$ C. by circulating the superfusate through a thermostatically controlled water bath immediately prior to entering the tissue chamber.

The preparations were stimulated through bipolar Teflon-coated platinum wires, bared at the tips, placed on the endocardial surface of the attached myocardium, using a W.P.I. digital stimulator set to deliver constant current pulses 1-2 msec. in duration at cycle lengths (c.l.) of 330 or 1000 msec. Stimulus strength was set at approximately 2x diastolic threshold, and adjusted as required through the experiment. All preparations were allowed to equilibrate in the tissue chamber for at least 1 hour before measurements were begun. Subsequently, a minimum of 60 minutes was allowed for equilibration with each drug-containing superfusate before post-drug measurements were made. Impalements were made at 5-10 sites throughout the preparation before and after drug exposure. Offset potentials were re-checked at the conclusion of each experiment.

Glass microelectrodes filled with 3M KCl were coupled to high impedance negative capacitance electrometers (W.P. Instruments, New Haven, CT), and Ag-/AgCl half-cells used as reference electrodes. The first derivative of the action potential upstroke ($\dot{V}$max) was obtained using an analog differentiator circuit, coupled to a peak-hold circuit that retained the recorded value of $\dot{V}$max for 30-70 msec. Action potential and $\dot{V}$max tracings were displayed on a Tektronix storage oscilloscope, and photographed for later analysis. In addition, chart paper recordings of Vmax were obtained using the peak-hold device output.

Fresh stock solutions of drug were prepared for each experiment. Compounds were dissolved in distilled water at total concentrations of 1-10 mg/ml, and subsequently diluted to a final concentration of 3 μm in appropriate volumes of normal Tyrode's solution for evaluation.

Action potential (AP) parameters measured included: diastolic take-off potential (or activation voltage, $V_{act}$); AP overshoot ($V_{os}$); AP duration measured as the time taken to repolarize to $-20$ mV ($APD_{20}$), $-60$ mV ($APD_{60}$), and $-80$ mV ($APD_{80}$); and maximal upstroke velocity ($\dot{V}$max). Data were compared using a two-sample t-test, with statistical significance taken as $p<0.05$. A significant rate-dependent change in $\dot{V}$max with or in the absence of changes in APD was taken, by definition, to indicate Class I anti-arrhythmic activity, while significant and uniform increases in $APD_{20}$, $APD_{60}$ and $APD_{80}$ without alterations in $\dot{V}max$ indicated Class III activity.

Based upon the activity profile elicited by the compounds of this invention in the above-described standard scientifically recognized test models, the compounds are established as anti-arrhythmic agents useful in the treatment of cardiac arrhythmias and conditions characterized by coronary arteries vasospasm and ischemia. For that purpose, the compounds may be administered orally or parenterally in suitable dosage forms compatable with the route of administration, whether oral, intraperitoneal, intramuscular, intravenous, intranasal, buccal, etc. The effective dose range determined in the animal test models has been established at from about 2 to about 20 milligrams per kilogram host body weight (preferably from 2 to 10 mg/kg) i.v., and from about 40 to about 100 mg/kg (preferably 40 to 50 mg/kg) p.o., to be administered in single or plural doses as needed to relieve the arrhythmatic dysfunction. The specific dosage regimen for a given patient will depend upon age, pathological state, severity of dysfunction, size of the patient, etc. Oral administration is performed with either a liquid or solid dosage unit in any conventional form such as tablets, capsules, solutions, etc., which comprise a unit dose (e.g. from about 2 milligrams to about 100 milligrams) of the active ingredient alone or in combination with adjuvants needed for conventional coating, tableting, solubilizing, flavoring or coloring. Parenteral administration with liquid unit dosage forms may be via sterile solutions or suspensions in aqueous or oleagenous medium. Isotonic aqueous vehicle for injection is preferred with or without stabilizers, preservatives and emulsifiers.

The following examples illustrate the preparation of a representative number of compounds of this invention. After each example, the change in action potential duration and upstroke velocity, where tested, are provided.

EXAMPLE 1

N-[4-[[[2-[bis(1-methylethyl)amino]ethyl](1-methylethyl)amino]sulfonyl]phenyl]-1,1,1-trifluoroacetamide p-Nitrobenzenesulfonyl chloride was reacted with N,N',N'-triisopropyl ethylene diamine to obtain the free base of N-[2-[bis(1-methylethyl)amino]ethyl]-N-(1-methylethyl)-4-nitrobenzene sulfonamide as a yellow solid, m.r. 98°–100° C.

Analysis for: $C_{17}H_{29}N_3O_4S$, Calculated: C, 54.96; H, 7.87; N, 11.31, Found: C, 54.43; H, 7.67; N, 11.66.

The product of the preceding paragraph was reduced catalytically in the system $Pt/H_2$/tetrahydrofuran. 4-Amino-N-[2-[bis(1-methylethyl)amino]ethyl]-N-(1-methylethyl)benzenesulfonamide ws isolated from the product mixture and crystallized from isopropanol, m.r. 100°–102° C.

Analysis for: $C_{17}H_{31}N_3O_2S$, Calculated: C, 59.79; H, 9.15; N, 12.30, Found: C, 59.54; H, 9.16; N, 12.22.

4-Amino-N-[2-[bis(1-methylethyl)amino]ethyl]-N-(1-methylethyl)benzene sulfonamide (4.0 grams) (0.0117 moles) in $Ch_2Cl_2$ (80 ml) containing triethylamine (1.41 g., 0.14 m.) was treated dropwise (from a hyperdermic syringe) with trifluoroacetic anhydride (2.94 g., 1.98 ml, 0.014 m.) at ice bath temperature. After 0.5 hours, the solution was washed with aqueous sodium bicarbonate and the solvent was removed to give a yellow gum. Treatment with isopropanol/HCl provided the title compound as the hydrochloride salt 5.16 g, m.r. 245°–247° C. (d).

Analysis for: $C_{19}H_{30}F_3O_3N_3S.HCl$, Calculated: C, 48.15; H, 6.38; N, 8.87, Found: C, 47.99; H, 6.63; N, 8.51 3 μM, 1000 msec. c.l.: %$\Delta APD_{60}$=+33.5; %$\Delta \dot{V}max$=−24.7.

EXAMPLE 2

N-[2-[bis(1-methylethyl)amino]ethyl]-4-[(trifluoroacetyl)amino]benzenesulfonamide p-Nitrobenzenesulfonyl chloride was reacted with N,N-diisopropyl ethylene diamine to give N-[2-[bis(1-methylethyl)amino]ethyl]-4-nitrobenzene sulfonamide as the free base, m.r. 86°–88° C.

Analysis for: $C_{14}H_{23}N_3O_4S$, Calculated: C, 51.05; H, 7.04; N, 12.76, Found: C, 51.34; H, 7.15; N, 12.66.

The product of the preceding paragraph was catalytically reduced in methanol/$PtO_2$ to provide 4-amino-N-[2-[bis(1-methylethyl)amino]ethyl]benzenesulfonamide, m.r. 115°–117° 1 C.

Analysis for: $C_{14}H_{25}N_3O_2S$, Calculated: C, 56,16; H, 8.42; N, 14.03, Found: C, 56.23; H, 8.46; N, 14.10.

4-Amino-N-[2-[bis(1-methylethyl)amino]ethyl]benzenesulfonamide (4.0 g., 0.0134 m.) in $CH_2Cl_2$ (50 ml.) and triethylamine (1.35 g., 0.0134 m.) was chilled in an ice bath and trifluoroacetic anhydride (2.81 g., 0.0134 m., 1.89 ml.) was added dropwise with stirring. The reaction was stored one hour at room temperature, washed with aqueous sodium bicarbonate and the solvent removed to give the crude free base. Conversion to the hydrochloride salt with IPA/HCl and recrystallization from isopropanol/methanol gave the crude hydrochloride salt. Preparative high performance liquid chromatography gave the product 0.700 g, m.r. 223°–225° C.

Analysis for: $C_{16}H_{24}F_3O_3N_3S.HCl$, Calculated: C, 44.50; H, 5.83; N, 9.73, Found: C, 44.50; H, 5.80; N, 9.51 3 μM, 1000 msec. c.l.: %$\Delta APD_{60}$=+4.0; %$\Delta \dot{V}max$=−6.2.

EXAMPLE 3

N-(1-methylethylN-[3-(1-methylethylamino]propyl4[(-trifluoroacetyl)amino]benzenesulfonamide, hydrochloride, ⅔ isopropanol Chlorosulfonic acid (100 g.) was cooled to 0° C. and trifluoroacetanilide (30 g.) was added portionwise with vigorous stirring keeping the temperature below +5° C. The reaction was stirred at room temperature overnight, and cautiously poured onto ice. The white solid produced was filtered, washed copiously with water, and dried to give 4-trifluoroacetamido benzenesulfonyl chloride (39.14 gl)(m.r. 143°–146° C.).

Analysis for: $C_8H_5ClF_3O_3NS$, Calculated: C, 33.41; H, 1.75; N, 4.87, Found: C, 33,34; H, 1.65; N, 4.82.

4-Trifluoroacetamido benzenesulfonyl chloride (10 g., 0.035 m.) was added portionwise to N,N¹-diisopropyl propane, 1,3-diamine (11.06 g.) in $CH_2Cl_2$ (300 ml.0 with stirring over one hour. The precipitated produce free base (8.56 g., m.r. 147°–149° C.) was dissolved in isopropanol and treated with isopropanol/HCl to provide the title compound in beautiful white flakes (8.51 g., m.r. 115°–118° C. (d)) as the hydrochloride salt, isopropanol solvate.

Analysis for: $C_{17}H_{26}F_3N_3O_3S.HCl/⅔ C_3H_8O$, Calculated: C, 47.48; H, 6,78; N, 8.74, Found: C, 47.10; H, 6.98; N, 8.41 3 μM, 1000 msec. c.l.: %$\Delta APD_{60}$=−15.8; %$\Delta \dot{V}max$=−15.2.

EXAMPLE 4

N-[4-[bis(1-methylethyl)amino]butyl-4[(trifluoroacetyl)amino]benzenesulfonamide

4-Trifluoroacetamido benzenesulfonyl chloride (10 g., 0.035 m.) was added portionwise to N,N-diisopropyl butane, 1,4-diamine (6.03 g., 0.035 m.) and triethylamine (3.54 g., 0.035 m.) in $CH_2Cl_2$ (300 ml.). The solution was washed with aqueous $K_2CO_3$ and stripped to provide a solid (11.29 g., m.r. 140°–142° C.)

Analysis for: $C_{18}H_{28}F_3O_3N_3S$, Calculated: C, 51.05; H, 6.66, N, 9.92, Found: C, 51.00; H, 6.80; N, 9.69.

The above free base was dissolved in boiling isopropanol made acid with isopropanol/HCl, cooled and diluted with five volumes of diethyl ether to provide the hydrochloride salt as an isopropanol solvate, off white flakes (10.89 g., m.r. 139°–142° C.).

Analysis for: $C_{18}H_{28}F_3O_3N_3S \cdot HCl \cdot \frac{1}{2}C_3H_8O$, Calculated: C, 47.59; H, 6.80; N, 8.61, Found: C, 47.58; H, 6.91; N, 8.63 3 μM, 1000 msec. c.l.: %ΔAPD$_{60}$=+2.0; %ΔVmax=+2.0.

EXAMPLE 5

N-[1-methylethyl]-N-[2-(1-methylethyl)amino-ethyl 4-[(trifluoroacetyl)-amino]-benzenesulfonamide 4-Trifluoroacetamido benzenesulfonyl chloride (10 g., 0.035 m.) was added portionwise with stirring to N,N$^1$-diisopropyl ethylene diamine (10.1 g., 0.07 m.) in $CH_2Cl_2$ (300 ml.) over one hour. The solution was washed with aqueous $K_2CO_3$ and the solvent removed to provide the crude produce as a gum. This material was chromatographed twice on dry column silica gel with 10% methanol/ethyl acetate to give the title compound as a white glass. This material was dissolved in isopropanol/HCl, the small amount of cloudy precipitate removed by filtration three Supercel and the filtrate was diluted with ten volumes of diethyl ether. The crystallized product was filtered and dried to give the hydrochloride salt of the title compound (3.35 g., m.r. 215°–217° C.).

Analysis for: $C_{16}H_{24}F_3O_3N_3S+HCl$, Calculated: C, 44.39; H, 5.82; N, 9.70, Found: C, 44.75; H, 5.80; N, 9.34 3 μM, 1000 msec. c.l.: %ΔAPD$_{60}$=+10.4; %ΔVmax=−9.3.

What is claimed is:
1. A compound of the formula:

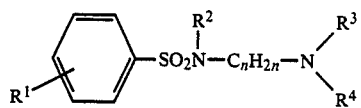

in which

R$^1$ is perfluoroalkanoylamino of 2 to 4 carbon atoms, in 3- or 4-position of the benzene ring;

R$^2$ is hydrogen or alkyl of 1 to 4 carbon atoms;

R$^3$ is hydrogen or straight or branched chain alkyl of 1 to 4 carbon atoms;

R$^4$ is straight or branched chain alkyl of 1 to 4 carbon atoms; and n is one of the integers 2, 3 or 4;

or a pharmaceutically acceptable salt thereof.

2. A compound of claim 1 which is N-[4-[[[2-[bis(1-methylethyl)amino]ethyl](1-methylethyl)amino]sulfonyl]phenyl]-1,1,1-trifluoroacetamido, or a pharmaceutically acceptable salt thereof.

3. A compound of claim 1 which is N-[2-[bis(1-methylethyl)amino]ethyl-4-[(trifluoroacetyl)amino]benzenesulfonamide, or a pharmaceutically acceptable salt thereof.

4. A compound of claim 1 which is N-(1-methylethyl)N-[3-(1-methylethyl amino]propyl-4[(trifluoroacetyl)amino]benzenesulfonamide, hydrochloride, ⅔ isopropanol, or a pharmaceutically acceptable salt thereof.

5. A compound of claim 1 which is N-[4-[bis(1-methylethyl)amino]butyl4[trifluoracetyl)amino]benzenesulfonamide, or a pharmaceutically acceptable salt thereof.

6. A compound of claim 1 which is N-[1-methylethyl]-N-[2-(1-methyl ethyl)amino]-ethyl-4-[(trifluoroacetyl)-amino]-benzenesulfonamide, or a pharmaceutically acceptable salt thereof.

* * * * *